United States Patent [19]
Van Antwerp et al.

[11] Patent Number: 5,807,315
[45] Date of Patent: Sep. 15, 1998

[54] METHODS AND DEVICES FOR THE DELIVERY OF MONOMERIC PROTEINS

[75] Inventors: William P. Van Antwerp; Nannette Van Antwerp, both of Valencia, Calif.

[73] Assignee: MiniMed, Inc., Sylmar, Calif.

[21] Appl. No.: 747,923

[22] Filed: Nov. 12, 1996

Related U.S. Application Data

[60] Provisional application No. 60/006,611, Nov. 13, 1995.

[51] Int. Cl.$^6$ .................................................. A61M 31/00
[52] U.S. Cl. .............................. 604/49; 604/85; 210/638; 210/651; 210/500.21; 530/304; 514/3
[58] Field of Search ........................ 604/4–6, 49, 51–54, 604/83, 85; 424/DIG. 6; 514/866, 3; 210/638, 651, 502.1, 500.27, 500.21, 321.6; 435/336; 530/304

[56] References Cited

U.S. PATENT DOCUMENTS

| | | | |
|---|---|---|---|
| 507,885 | 4/1893 | Matsumura | 210/632 |
| 4,183,849 | 1/1980 | Hansen et al. | 260/112.7 |
| 4,459,226 | 7/1984 | Grimes et al. | 260/112.7 |
| 4,861,705 | 8/1989 | Margel | 435/2 |
| 4,931,498 | 6/1990 | Pidgeon | 525/54.1 |
| 4,940,456 | 7/1990 | Sibalis et al. | 604/20 |
| 5,130,298 | 7/1992 | Cini et al. | 514/12 |
| 5,505,713 | 4/1996 | Van Antwerp . | |
| 5,538,511 | 7/1996 | Van Antwerp . | |
| 5,587,060 | 12/1996 | Abe et al. | 214/554 |
| 5,597,485 | 1/1997 | Mazza et al. | 210/635 |
| 5,597,796 | 1/1997 | Brange | 514/3 |

FOREIGN PATENT DOCUMENTS

| | | | |
|---|---|---|---|
| 2 114 573 | 8/1983 | United Kingdom | C07C 103/52 |

OTHER PUBLICATIONS

Harlow, E. et al., *Antibodies: A Laboratory Manual* Cold Spring Harbor Laboratory, New York, pp. 521–538 (1988).

Krejci, I. et al., "Transport of $Zn(OH)_4^{-2}$ Ions across a Polyolefin Microporous Membrane," *J. Electrochem. Soc.* 140(8):2279–2283 (1993).

Sluzky, V. et al., "Kinetics of insulin aggregation in aqueous solutions upon agitation in the presence of hydrophobic surfaces," *Proc. Natl. Acad. Sci. U.S.A.* 88:9377–9381 (1991).

Tierney, M.J. et al., "Electroreleasing Composite Membranes for Delivery of Insulin and Other Biomacromolecules," *J. Electrochemical Society*, 137(6):2005–2006 (1990).

*Primary Examiner*—Michael Powell Buiz
*Assistant Examiner*—Chalin Smith
*Attorney, Agent, or Firm*—Townsend and Townsend and Crew LLP

[57] ABSTRACT

Methods and devices for dissociating multimeric proteins and their delivery to patients, along with resultant compositions, are provided. A monomeric protein delivery device is also provided, comprising a supply of a multimeric protein 4, complex, comprising multimeric protein and an aggregating agent; a flow path having a subcutaneous exit 8, fluidly coupling the multimeric protein supply to the exit; a porous surface assembly situated along the flow path comprising a porous surface 10; and an aggregating agent binding partner carried by the surface 12; whereby the aggregating agent of the multimeric protein complex passing along the surface is bound to the binding partner on the surface to create a monomeric protein flow through the subcutaneous exit.

25 Claims, 2 Drawing Sheets

5,807,315

METHODS AND DEVICES FOR THE DELIVERY OF MONOMERIC PROTEINS

This application claims the benefit of U.S. provisional application Ser. No. 60/006,611 filed Nov. 13, 1995, hereby incorporated by reference in its entirety.

BACKGROUND OF THE INVENTION

Insulin exists in solution as a monomer in equilibrium with dimers and hexamers. When these forms are administered to a patient, the multimeric forms must dissociate in the body to a monomeric form, which is then absorbed by capillaries in the body. This is disadvantageous in situations where a patient must "plan ahead" to the time insulin is actually required by the body. For example, a patient must give himself or herself a "meal bolus" of regular insulin 25 to 40 minutes before each meal.

Pumps (e.g., Minimed) are available for delivery of insulin to a patient, whereby microinfusions of insulin can be delivered in a programmable fashion to a patient. Although these microinfusions reduce the need for administering a meal bolus in advance of a meal, there is still a delay in absorption of the hexameric insulin delivered.

Thus, there exists a need for a method for delivering monomeric insulin to a patient. The instant invention addresses this problem and more.

SUMMARY OF THE INVENTION

One aspect of the invention is a method of delivering a monomeric protein preparation to a patient comprising
  (a) providing a surface coated with a binding partner for an aggregating agent, the aggregating agent being present in a preparation of a multimeric protein; and
  (b) administering a preparation of the multimeric protein to the patient via the surface of step (a), whereby the aggregating agent in the multimeric preparation binds to the binding partner on the surface and the multimeric protein is dissociated into monomers.

A further aspect of the invention is a method for dissociating a multimeric insulin complex, method comprising:
  (a) binding a zinc chelating agent to a surface;
  (b) contacting the surface with the multimeric insulin complex, whereby zinc binds to the chelating agent and the multimeric insulin is dissociated into monomers; and
  (c) recovering monomeric insulin generated by step (b).

A further aspect of the invention is a method of delivering monomeric insulin to a patient comprising:
  (a) providing a zinc chelating agent bound to a surface;
  (b) contacting the surface with multimeric insulin, whereby zinc binds to the chelating agent and the multimeric insulin is dissociated into monomers; and
  (c) delivering the monomeric insulin to a patient.

A further aspect of the invention is a monomeric protein delivery device comprising:
  a supply of a multimeric protein complex, comprising multimeric protein and an aggregating agent;
  a flow path having a subcutaneous exit, fluidly coupling the multimeric protein supply to the exit; and
  a carrier surface assembly situated along the flow path comprising
    a carrier surface; and
    an aggregating agent binding partner carried by the carrier surface;

whereby the aggregating agent of the multimeric protein complex contacting the carrier surface is bound to the binding partner on the surface to create a monomeric protein flow through the subcutaneous exit.

DESCRIPTION OF THE PREFERRED EMBODIMENT

Figure 1:
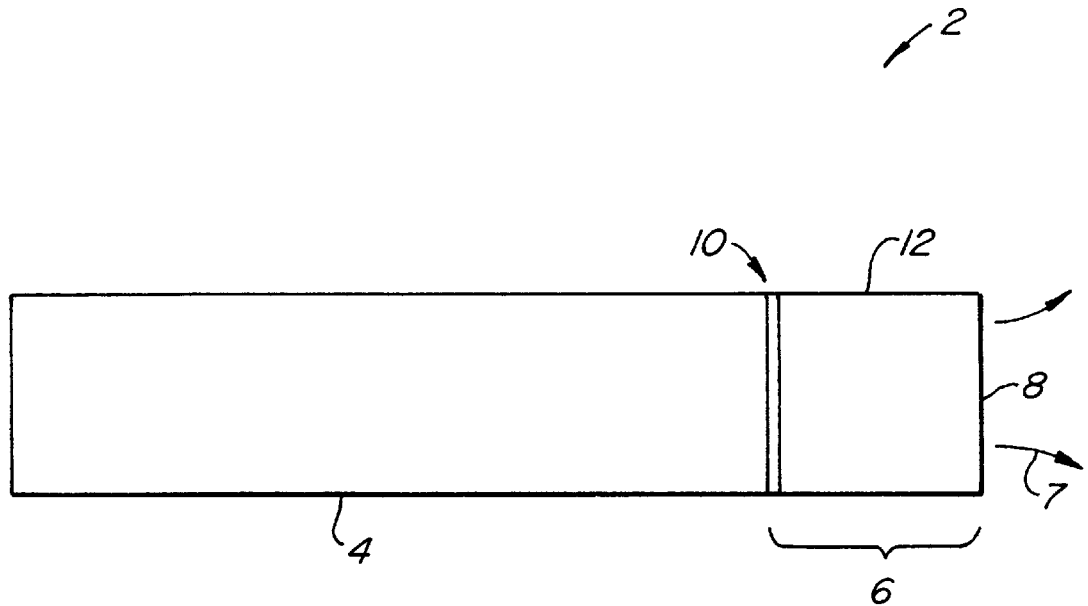
FIG. 1 is a schematic drawing of a device for delivering monomeric protein.

The instant invention provided a general method for dissociating multimeric proteins into monomeric components or subunits by reducing or removing an aggregating agent from a preparation of the multimeric protein. Thus, "aggregating agent" as used herein, refers to a compound, such as a metal ion, required for monomeric subunits of a protein to associate as a multimer. "Aggregating agent" agents which cause the undesirable non-specific association of monomer or multimers of proteins are also included in the scope of the invention. Some examples of aggregating agents include but are not limited to aluminum, calcium, magnesium, zinc, albumin, protamine, antibodies, ligands (including genetic engineered polypeptides, etc.).

Typically, the aggregating agent is removed via a binding partner, such as a chelating agent, antibody, ligand, or receptor. The binding partner typically has an affinity for the aggregating agent of at least twofold, preferably two to tenfold or greater than that of the protein monomer for the aggregating agent. The binding partner is typically immobilized on a carrier surface, such as a matrix or membrane, such that when the protein preparation passed through the matrix the aggregating agent is bound to the binding partner. The surface can be coated with the binding partner or the binding partner immobilized to the surface or conjugated to the surface or be incorporated as an integral part of the surface by a variety of techniques well known in the art (e.g., Harlow et al., *Antibodies: A Laboratory Manual*, pp. 521–538, Cold Spring Harbor Press, Cold Spring Harbor, N.Y. (1988); U.S. Pat. No. 5,505,713; U.S. Pat. No. 5,538,511).

In an embodiment, the surface is a membrane. The membrane typically has pore sizes of a suitable size for monomeric protein to pass through. The pore size is chosen on the basis of the molecular weight of the monomeric protein of interest. Typically, pore sizes in membranes are described in ranges. Thus, for a given protein of an average molecular weight for a monomer, a preferred range of pore sizes would be 20–50% smaller to 20–50% larger than the average molecular weight of the monomer. Thus, for example, a preferred pore size for insulin monomers would be about 4000 to about 20,000MW, more preferably about 4000 to 8000MW. Typical membranes include cellulose, acetate, polysulfone, teflon, or other membranes having a polymeric backbone with holes or pores of a particular size range. In some embodiments, the membrane can be bonded to a cross-section of a catheter by any means known in the art, such as with heat, adhesives, or solvents, or may be mounted on the end of a catheter with a retaining means, such as a retaining ring.

For example, the surface of a polysulfone membrane (W. R. Grace) having a 10,000MW cutoff, is rendered acidic by soaking the membrane in nitric or sulfuric acid for 30 minutes. Insulin is then passed through the membrane. Insulin at the membrane is destabilized and dissociated into monomers by the chelation of zinc. The monomer easily passes through the membrane, whereas hexamers cannot so diffuse. Once the surface is coated with zinc ions, it continues to act as an ion-exchange membrane, further destabilizing insulin as long as there are active surface sites available for attraction of zinc ions. This is because the rate of dimerization of insulin is slow compared to the rate of diffusion through the membrane. The preferential passage of monomers through the membrane can be verified by capillary electrophoresis.

In an embodiment, the surface or matrix is a component of a catheter made from a porous material which allows monomeric protein to diffuse out of a predetermined length of the catheter. Typically, such a device is implanted in a patient.

In some embodiments, the surface or matrix can be a component of a catheter or a fitting on a catheter. The catheter may be external to the patient or may be implanted in the patient. A typical catheter is silicone rubber having an internal dimension of about 0.07 inch and an external dimension of about 0.110 inch. In some embodiments, the protein is pumped through the catheter. The pump can be external to the patient or implanted. Exemplary pumps include but are not limited to MiniMed Model 507 and MiniMed 2001.

In some embodiments, the matrix, or contacting medium, coated with a binding partner, is used to fill or pack the lumen of a catheter. The protein preparation is passed through the matrix packed catheter, thereby coming in contact with the binding partner.

In some embodiments, insulin is the preferred protein. The aggregating agent in insulin preparations is zinc. The binding partner for zinc ion is typically a chelating agent, such as but not limited to oxygen containing chelators such as organic alcohols and ethers, non-acetic acid amines such as triethylamine and ethylene diamine, phosphorus containing ligands such as phoshines and sulfur based ligands such as organic sulfonates, triethylenetetramine, tetraethylenepentamine, nitriloacetic acid, ethylenediamine-tetraacetic acid; N-hydroxyethylenediaminetriacetic acid, ethyletherdiaminetetracetic acid, ethyleneglycol-bis-beta-aminoethylether)N—N tetracetic acid, diethylene triamine pentaacetic acid, and cyclohexanediamine tetracetic acid. For an implantable pump or catheter system, a preferred chelator would preferably bind the aggregating agent with about a factor of two-fold greater than that of insulin for the aggregating agent. In a preferred embodiment, Nafion® (Krejci, I. et al., *J. Electrochem. Soc.*, 140:2279 (1993)) is used as the binding partner on the surface or matrix.

Any commercial insulin preparation can be used in this method for preparing monomeric insulin, including but not limited to HUMULIN R™, VELOSIN BR™, and HOE21pH U400 and U100 (Hoechst). Preferably, the insulin is the commonly termed "regular" insulin. The insulin may be prepared in any buffer or in any aqueous formulation, including sterile water.

In some embodiments, the flow rate through the matrix, contacting medium, or membrane, is typically about 100 µl to 2 ml/day.

As an example of the advantages of the invention, the dynamics of insulin absorption in the body can be described as follows. Insulin hexamer is dissociated to insulin dimer, and then to insulin monomer, as described by the following equation 1 (Sluzky et al. *Proc Natl. Acad. Sci.* 88: 9377–9381 (1991)):

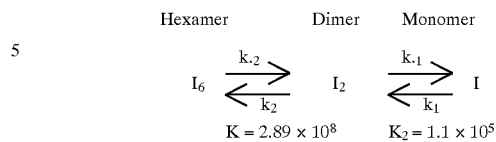

The local concentration gradient in the patient's tissue drives the equilibrium process according to Le Chatelier's principle. Only monomeric insulin can be absorbed by the capillaries. As the local concentration of monomer decreases by adsorption to the capillaries, the equilibrium shown in Equation 1 shifts to the right as follows in Equation 2:

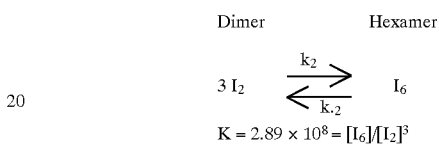

Thus, the rate of insulin absorption can be increased in a patient to whom a monomeric insulin has been provided. Similarly, other proteins can be delivered to a patient by the method of the invention to increase rate of absorption, or otherwise enhance therapeutic use of the protein.

An embodiment of the invention is the use of a device having a binding partner specific for an aggregating agent to prepare monomeric protein by contacting the device with a multimeric protein preparation comprising an aggregating agent, thereby binding the aggregating agent to the binding partner and causing dissociation of the multimeric protein onto monomers. The monomers are typically generated during delivery of the protein preparation to the patient.

Other embodiments of the invention include a monomeric protein delivery device 2. The delivery device 2, depicted in FIG. 1, will typically comprise a supply 4 of a multimeric protein, comprising multimeric protein and an aggregating agent; a flow path 6 having a subcutaneous exit 8, fluidly coupling the multimeric protein supply 4 to the exit 8; and a carrier surface assembly 10 situated along the flow path. The carrier surface assembly 10 comprises a carrier surface, typically a porous matrix 12, and an aggregating agent binding partner carried by the porous matrix. The aggregating agent of the multimeric protein complex passing along the surface is bound to the binding partner on the porous matrix to create a monomeric protein flow 7 through the subcutaneous exit 8. "Subcutaneous" as used herein refers any location below the skin. In some embodiments the multimeric protein complex preferably comprises a supply of multimeric insulin. The binding partner, can be a chelating agent, as described above, and in some embodiment is preferably Nafion®. The aggregating agent, as described above, is preferably zinc in some embodiments.

Figure 2:
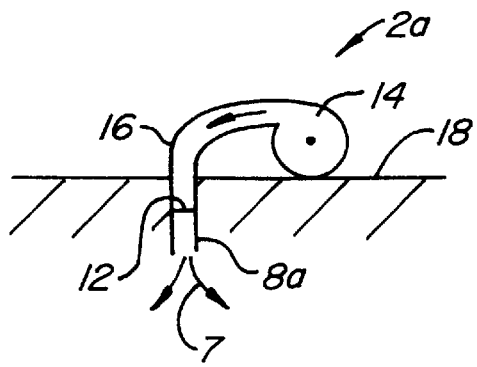
FIGS. 2–5 are simplified views of four embodiments of the device of FIG. 1.

FIG. 2 illustrates an alternative embodiment of the device 2 of FIG. 1 with like reference numerals referring to like elements. Device 2a comprises a pump 14, such as a microinfusion pump made by MiniMed Inc. of Sylmar, Calif. or HTRON-100 made by Disetronics of Switzerland. Pump 14 includes the supply of a multimeric protein. Pump 14 is coupled to a catheter 16 having a subcutaneous exit 8a at its distal end, exit 8a being situated beneath skin 18 of the patient.

Figure 3:
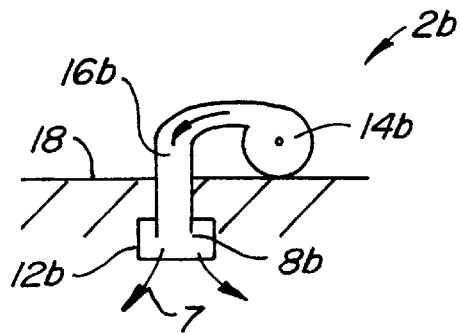
Figure 4:
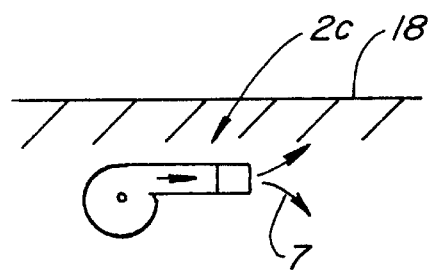
Figure 5:
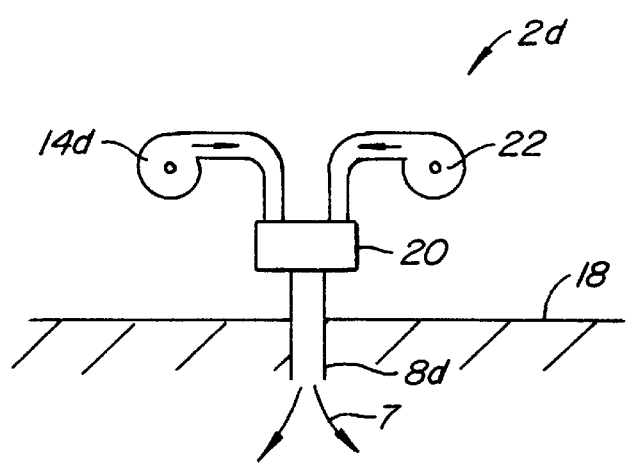

FIG. 3 illustrates an alternative to the device 2a of FIG. 2. Device 2b replaces porous matrix 12, which is situated along the length of catheter 16 of device 2a, by a porous matrix cap 12b surrounding exit 8b. Either of device 2a or 2b could be implanted beneath skin 18 as suggested by device 2c in FIG. 4. FIG. 5 illustrates a further alternative in which the protein preparation and binding partner are provided in separate reservoirs (14d, 22), then mixed in compartment 20 before exiting subcutaneously (8d).

Other types of pumps, such as a manually actuated syringe-type pumps, could also be used, as can pumps which use hydrostatic forces generated across a semipermeable membrane.

EXAMPLE

Figure 6:
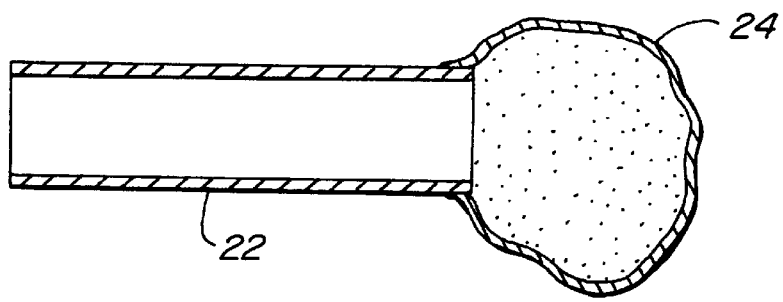
FIG. 6 is a schematic drawing of a device for delivering monomeric proteins comprising a catheter and a diffusion membrane mounted at one end.

A device for generating insulin monomers was generated as follows. A polysulfone dialysis membrane (W. R. Grace) having a MW cut-off of about 10,000 was presoaked in EDTA, then sonically bonded to the end of a silicon rubber (Nusil). The catheter had an internal dimension of 0.07 inch and an external dimension of 0.110 inch. catheter with heat. A commercial preparation of insulin was passed through the membrane and the resulting preparation analyzed by capillary electrophoresis to confirm the presence of insulin monomers. The device, depicted in FIG. 6, comprises a catheter 22 and a diffusion membrane 24 mounted to one end.

All references cited herein are incorporated by reference in their entirety for all purposes.

What is claimed is:

1. A method of delivering a monomeric protein preparation to a patient comprising:
   (a) providing a surface coated with a binding partner for an aggregating agent, the aggregating agent being present in the preparation of the multimeric protein; and
   (b) administering the preparation of the multimeric protein to the patient via the surface of step (a), whereby the aggregating agent in the multimeric preparation binds to the binding partner on the surface and the multimeric protein is dissociated into monomers.

2. The method of claim 1, wherein the protein is insulin.

3. The method of claim 1 wherein the aggregating agent is zinc.

4. The method of claim 1, wherein the protein is pumped through the surface.

5. The method of claim 1, wherein the surface is implantable.

6. The method of claim 1 wherein the binding partner is a chelating agent.

7. The method of claim 6, wherein the chelating agent is an ion exchange medium.

8. The method of claim 1, wherein the surface is a membrane.

9. The method of claim 8, wherein the membrane comprises pores of about 4000 to about 20,000MW.

10. A method of delivering monomeric insulin to a patient comprising:
    (a) providing a zinc chelating agent bound to a surface;
    (b) contacting the surface with multimeric insulin, whereby zinc binds to the chelating agent and the multimeric insulin is dissociated into monomers; and
    (c) delivering the monomeric insulin to a patient.

11. A method for dissociating a multimeric insulin complex, method comprising:
    (a) binding a zinc chelating agent to a surface;
    (b) contacting the surface with the multimeric insulin complex, whereby zinc binds to the chelating agent and the multimeric insulin is dissociated into monomers; and
    (c) recovering monomeric insulin generated by step (b).

12. The method of claim 11, wherein the surface is implantable.

13. The method of claim 11, wherein the monomeric protein is administered to a patient.

14. The method of claim 13, wherein the monomeric protein is administered to a patient via a pump.

15. A monomeric protein delivery device comprising:
    a supply of a multimeric protein complex, comprising multimeric protein and an aggregating agent;
    a flow path having a subcutaneous exit, fluidly coupling the multimeric protein supply to the exit; and
    a carrier surface assembly situated along the flow path comprising:
        a carrier surface; and
        an aggregating agent binding partner carried by the carrier surface;
    whereby the aggregating agent of the multimeric protein complex contacting the carrier surface is bound to the binding partner on the carrier surface to create a monomeric protein flow through the subcutaneous exit.

16. The device according to claim 15, wherein the supply of multimeric protein complex comprises a supply of multimeric insulin.

17. The device according to claim 15, wherein the aggregating agent is zinc.

18. The device according to claim 15, wherein the flow path assembly comprises a catheter.

19. The device according to claim 15, wherein the binding partner is a chelating agent.

20. The device according to claim 19, wherein the chelating agent is Nafion.

21. The device according to claim 15, wherein the carrier surface comprises a porous matrix.

22. The device according to claim 21, wherein the porous matrix has a porosity of about 4000–20,000MW.

23. The device according to claim 15, wherein the flow path assembly comprises a pump for pumping the multimeric protein complex along the flow path.

24. The device according to claim 23, wherein the pump is external to a patient.

25. The device according to claim 23, wherein the pump implanted in a patient receiving the monomeric protein.

* * * * *